United States Patent [19]

Chan et al.

[11] Patent Number: 5,198,584

[45] Date of Patent: Mar. 30, 1993

[54] P-PHENYLENEDIAMINE SUBSTITUTED BY A QUATERNARY AMMONIUM GROUP AND AN ELECTRON WITHDRAWING GROUP

[75] Inventors: A. C. Chan, Mineola, N.Y.; Y. G. Pan, Stamford; D. L. Chang, Norwalk, both of Conn.

[73] Assignee: Clairol Inc., New York, N.Y.

[21] Appl. No.: 894,150

[22] Filed: Jun. 4, 1992

Related U.S. Application Data

[62] Division of Ser. No. 798,452, Nov. 27, 1991, Pat. No. 5,139,532.

[51] Int. Cl.$^5$ ........................ C07C 211/00; A61K 7/13
[52] U.S. Cl. ........................... 564/289; 8/405; 8/406; 8/407; 8/408; 8/410; 8/414; 8/416; 8/423; 424/70; 558/422; 562/36; 564/282; 564/285; 564/287
[58] Field of Search ............... 564/282, 285, 287, 289; 558/422; 562/36

[56] References Cited

FOREIGN PATENT DOCUMENTS 0355735 2/1990 European Pat. Off. .
1292784 4/1969 Fed. Rep. of Germany .
2018453 4/1979 United Kingdom .

OTHER PUBLICATIONS

Berth et al., "Nitro, Ozo, and Anthraquinone Dyes, etc.", *J. Soc. Cosmet. Chem.* 18(12), 705-713 cited in *Chem. Abst.* CA 68(8):33094r.

*Primary Examiner*—Allen J. Robinson
*Assistant Examiner*—P. O'Sullivan
*Attorney, Agent, or Firm*—Morton S. Simon

[57] ABSTRACT p-phenylenediamines having a quaternary ammonium group and substituted with an electron withdrawing group, derivatives thereof, compositions containing same, and their use as developers for dyeing keratinous fibers, are disclosed.

7 Claims, No Drawings

P-PHENYLENEDIAMINE SUBSTITUTED BY A QUATERNARY AMMONIUM GROUP AND AN ELECTRON WITHDRAWING GROUP

RELATED APPLICATIONS

This is a divisional of application Ser. No. 07/798,452 filed Nov. 27, 1991, now U.S. Pat. No. 5,139,532.

We have found (and demonstrate in our Examples) that such compounds produce extremely weak colors on hair.

p-phenylenediamines bearing an electron withdrawing group would be expected to react slowly in an oxidative dye system. Consequently, such compounds would not be expected to be useful as permanent hair dye precursors.

Surprisingly, applicants have found that the compounds of the present invention lead to more intense color than their non-quaternized analogs. Furthermore, they advantageously afford redder shades than conventional p-phenylenediamines.

SUMMARY OF THE INVENTION

Accordingly, one object of the present invention is to provide compounds of the formula I:

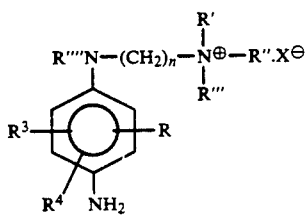

wherein:
n is an integer from 1 to 6;
$X^-$ is a halide or methylsulfate group;
R', R", R''' are each, independently, $C_{1-6}$ alkyl or $C_{1-6}$ (poly)hydroxyalkyl;
R'''' is hydrogen, $C_{1-6}$ alkyl or $C_{1-6}$ (poly)hydroxyalkyl;
R is an electron withdrawing group strong enough to substantially prevent the oxidation of the amino groups by conventional oxidative hair dyeing conditions; and
$R^3$ and $R^4$ are each, independently, hydrogen, $C_{1-6}$ alkyl, halogen, or $C_{1-6}$ alkoxy.

Another object of the present invention is to provide hair dyeing compositions containing compounds of the above formula I together with cosmetically acceptable carriers.

A third object of the present invention is to provide a process for dyeing keratinous fibers which comprises applying to hair a composition containing a tinctorially effective amount of a compound of formula I in a cosmetically acceptable carrier.

DETAILED DESCRIPTION OF THE INVENTION

The oxidation hair dye developers of the present invention are the compounds of the formula I:

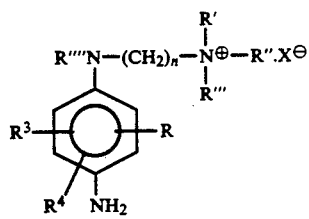

wherein:
n is an integer from 1 to 6;
$x^-$ is a halide or methylsulfate group;
R', R", R''' are each, independently, $C_{1-6}$ alkyl or $C_{1-6}$ (poly)hydroxyalkyl;
R'''' is hydrogen, $C_{1-6}$ alkyl or $C_{1-6}$ (poly)hydroxyalkyl;
R is an electron withdrawing group strong enough to substantially prevent the oxidation of the amino groups and;
$R^3$ and $R^4$ are each, independently, hydrogen, $C_{1-6}$ alkyl, or $C_{1-6}$ alkoxy.

As used herein:
"halogen" means chloride, bromide, iodide and fluoride.
"$C_{1-6}$ alkyl" means an alkyl chain, straight or branched, containing 1 to 6 carbon atoms, such as, methyl, ethyl, n- and iso-propyl, n-, sec- and tert-butyl, n-hexyl, and the like.
"$C_{1-6}$ (poly)hydroxyalkyl" means an alkyl chain, straight or branched, containing 1 to 6 carbon atoms, substituted by 1 to 3 hydroxy group(s), such as, 2-hydroxyethyl, 2,3-dihydroxy-n-propyl, 1,2,3-trihydroxy-n-propyl, and the like.
"$C_{1-6}$ alkoxy" means an alkyl chain, straight or branched, containing 1 to 6 carbon atoms and linked to the rest of the molecule by an —O— group.
"Strong enough to substantially prevent the oxidation of the amino groups" means that the group R substantially withdraws electron(s) from the phenyl ring so that the amino groups are substantially protected against oxidation when subjected to oxidative hair dyeing conditions so that the compound is not converted into the corresponding p-benzoquinonediimine when the quaternary side chain is not present in the molecule. Examples of suitable groups are F, $CF_3$, CN, and the like.

Preferred compounds of formula I are:
those wherein R is selected from the group consisting of F, $CF_3$ and CN;
those wherein n is equal to 2 or 3;
those wherein $X^-$ is iodide;
those wherein $R^3$ and $R^4$ are each, independently, hydrogen, $C_{1-3}$ alkyl, or halogen $C_{1-3}$ alkoxy;
those wherein R', R", and R''' are each, independently, $C_{1-3}$ alkyl; and
those wherein R'''' is hydrogen or methyl.

More preferred compounds are:
those wherein $R^3$ and $r^4$ are both hydrogen;
those wherein n is equal to 2;
those wherein R', R" and R''' are methyl; and
those wherein R'''' is hydrogen.

Most preferred compounds are selected from the group consisting of:
2-(4-amino-2-fluoroanilino)ethyltrimethylammonium iodide,
2-(4-amino-2-trifluoromethylanilino)ethyltrimethylammonium iodide, and 2-(4-amino-2-cyanoanilino)ethyltrimethylammonium iodide.

The present invention also provides dyeing compositions comprising:

a) a tinctorially effective amount of a compound of the formula I:

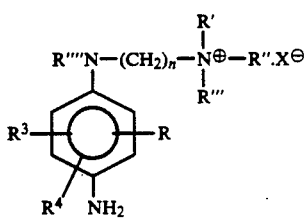

wherein:

n is an integer from 1 to 6;

$X^-$ is a halide or methylsulfate group;

$R'$, $R''$, $R'''$ are each, independently, $C_{1-6}$ alkyl or $C_{1-6}$ (poly)hydroxyalkyl;

$R''''$ is hydrogen, $C_{1-6}$ alkyl or $C_{1-6}$ (poly)hydroxyalkyl;

R is an electron withdrawing group strong enough to substantially prevent the oxidation of the amino groups; and $R^3$ and $R^4$ are each, independently, hydrogen $C_{1-6}$ alkyl, halogen or $C_{1-6}$ alkoxy; and b) a cosmetically acceptable carrier.

Preferred compositions are:

those employing compound of the formula I wherein R is selected from the group consisting of F, $CF_3$, and CN;

those employing compound of the formula I wherein n is 2 or 3;

those employing compound of the formula I wherein $X^-$ is iodide;

those employing compound of the formula I wherein $R^3$ and $R^4$ are each, independently, hydrogen, $C_{1-3}$ alkyl, halogen, or $C_{1-3}$ alkoxy;

those employing compound of the formula I wherein $R'$, $R''$, and $R'''$ are each, independently, $C_{1-3}$ alkyl; and those employing compound of the formula I wherein $R''''$ is hydrogen or methyl.

More preferred compositions are:

those employing compound of the formula I wherein $R^3$ and $R^4$ are hydrogen;

those employing compound of the formula 1 where n is 2;

those employing compound of the formula I wherein $R'$, $R''$ and $R'''$ are methyl; and those employing compound of the formula I wherein $R''''$ is hydrogen.

Most preferred compositions are:

those which employ as the compound of formula I 2-(4-amino-2-fluoroanilino) ethyltrimethylammonium iodide;

2-(4-amino-2-trifluoromethylanilino)ethyltrimethylammonium iodide; or 2-(4-amino-2-cyanoanilino)ethyltrimethylammonium iodide.

The pH of the composition of the present invention may vary from about 3 to about 11.

The concentration of the dye of the present invention employed in the dyeing composition of the invention may vary somewhat depending on the nature of the carrier, the presence of other hair dyes, the results desired, and the like. All that is required is that a tinctorially effective amount of the dye be employed. Generally, the dye of formula I will be present in said carrier at a concentration in the range of from about 0.01% to about 10%, preferably from about 0.1% to about 5%, by weight, based on the total weight of the dye composition. As used herein, the term "dyeing composition" means the total dyeing composition, including adjuvants and additives.

The cosmetically acceptable carriers employed in the dyeing compositions of the present invention may vary in complexity from simple solutions or dispersions, which employ aqueous or aqueous alcoholic solvents, to very complex systems. Thickened compositions may be employed as the carrier. Water will ordinarily constitute the major component of the dyeing compositions of the invention. The amount of water employed will vary widely depending on the types and quantity of adjuvants or additives contained in the composition. Thus, water may constitute as little as 10% by weight of the dyeing composition, based on the total weight of the dyeing composition. Usually it constitutes from about 70% to about 90% by weight, based on the total weight of the composition.

It is often advantageous to include in the dyeing compositions of the present invention an organic solvent or solvent system which helps solubilize the dyes and adjuvants contained therein. A number of organic solvents are known in the art that are useful for such purpose. These include alcohols, particularly alkyl alcohols of 1 to 6 carbons, especially ethanol, propanol, isopropanol and glycols of up to about 10 carbons, especially diethyleneglycol monoethyl ether; carbitols; and benzyl alcohol. When present, the solvents will constitute from about 1% to about 60%, preferably from about 10% to about 30% by weight based on the total weight of the dyeing composition.

The dyeing compositions of this invention may also contain other conventional adjuvants or additives commonly found in hair dye compositions. These include such items as surface active agents, thickening agents, alkalizing agents, chelating agents, perfumes, and the like.

The surface active agents are typically water soluble, less preferably, water dispersible, and include anionic, nonionic and cationic surface active agents. Illustrative of the various types of water soluble surface active agents that may be employed are: higher alkyl benzene sulfonates; alkyl naphthalene sulfonates; sulfonated esters of alcohols and polyacids; taurates; fatty alcohol sulfates; sulfates of branched chain or secondary alcohols; alkyl dimethylbenzylammonium chlorides, and the like.

Illustrative of surfactants that may be employed are: lauryl sulfate; polyoxyethylene lauryl ester; myristyl sulfate; glyceryl monostearate; sodium or potassium or ammonium salt of palmitic or oleic acid, methyl taurine; cetyl pyridinium chloride; lauryl sulfonate; myristyl sulfonate; lauric diethanolamide; polyoxyethylene stearate; stearyl dimethylbenzyl- ammonium chloride; dodecyl benzene sodium sulfonate; nonyl naphthalene sodium sulfonate; dioctyl sodium sulfosuccinate; sodium dodecyl sulfate, and the like. The quantity of water soluble surface active agent employed can vary widely up to about 15%. Preferably it is present in an amount of from about 0.10% to 10% by weight, based on the total weight of the composition.

The thickening agent, when employed, may be one or more of those commonly used in hair dyeing. Examples of suitable thickening agents are: sodium alginate; gum arabic; cellulose derivatives, such as methylcellulose and sodium carboxymethylcellulose; acrylic polymers, such as polyacrylic acid sodium salt; and inorganic thickeners, such as bentonite. The quantity of thickening agent employed can vary over a wide range. Typically the thickening agent is employed in an amount up to about 20%, preferably from about 0.1% to 5% by weight, based on the total weight of the composition.

The present compositions can also contain conventional oxidation couplers and their derivatives, in the presence of a conventional oxidizer such as hydrogen peroxide, to provide a range of shades on the keratinous fibers.

Preferred couplers are α-naphthol, m-aminophenol, m-phenylene diamine, resorcinol, 5-amino-o-cresol and 2,4-bis(hydroxyethoxy)-1,5-diaminobenzene. Similarly, the compositions can contain other conventional semi-permanent dyes, such as o- and p-nitroanilines, nitro-p-phenylenediamines, aminoanthraquinones, aminoazobenzenes, and their derivatives.

A third object of the present invention is to provide a process for dyeing a keratinous fiber which comprises applying to said keratinous fiber a dyeing composition comprising:

a) a tinctorially effective amount of a compound of formula I:

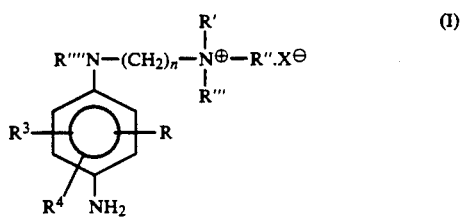

wherein
n is an integer from 1 to 6;
X⁻ is a halide or methylsulfate group;
R', R'', R''' are each, independently, $C_{1-6}$ alkyl or $C_{1-6}$ (poly)hydroxyalkyl;
R'''' is hydrogen, $C_{1-6}$ alkyl or $C_{1-6}$ (poly)hydroxyalkyl;
R is an electron withdrawing group strong enough to substantially prevent the oxidation of the amino groups; and
$R^3$ and $R^4$ are each independently, hydrogen, $C_{1-6}$ alkyl, halogen, or $C_{1-6}$ alkoxy; and b) a cosmetically acceptable carrier.

Preferred processes are:
those which employ a compound of formula I wherein R is selected from the group consisting of F, CF₃, and CN.
those which employ a compound of formula I wherein n is 2 or 3;
those which employ a compound of formula I wherein X⁻ is iodide;
those which employ a compound of formula I wherein $R_3$ and $R_4$ are each, independently, hydrogen, $C_{1-3}$ alkyl, halogen, or $C_{1-3}$ alkoxy;
those which employ a compound of formula I wherein R', R'', R''' are each, independently, $C_{1-3}$ alkyl; and
those which employ a compound of formula I wherein R'''' is hydrogen or methyl.

More preferred processes are:
those which employ a compound of formula I wherein $R_3$ and $R_4$ are hydrogen;
those which employ a compound of formula I where n is 2;
those which employ a compound of formula I wherein R', R'' and R''' are methyl; and
those which employ a compound of formula I wherein R'''' is hydrogen.

Most preferred processes are those which employ a compound of formula I selected from the group consisting of:
2-(4-amino-2-fluoroanilino)ethyltrimethylammonium iodide,
2-(4-amino-2-trifluoromethylanilino)ethyltrimethylammonium iodide, and
2-(4-amino-2-cyanoanilino)ethyltrimethylammonium iodide.

The dyeing composition used in the present processes may also contain conventional couplers, such as, α-naphthol, m-aminophenol, m-phenylenediamine, resorcinol, 5-amino-o-cresol, and the like. The dyeing composition may also contain one or more direct dyes and one or more oxidation dye intermediates.

In accordance with the process of the instant invention, the dyeing composition can be applied to living human hair on the head by conventional techniques known in the art. For example, they can be poured over the hair or applied with a brush, sponge, or other means of contact, until the hair is properly impregnated. The time of contact of the dyeing composition with the hair is not critical and can vary over the wide range used in the hair dyeing art. Usually such time ranges from about 5 minutes to 2 or more hours, preferably it is from about 10 to about 60 minutes. The dyeing of live hair is preferably effected at a temperature below 40° C., such as from 15° C. to 40° C. More preferably, it is effected at ambient temperature, e.g. about 20° C. to about 35° C.

The compounds of formula I may be prepared according to conventional methods known in the art.

The dyeing compositions of the present invention can be prepared by conventional methods used in the hair dyeing art. Thus, they can be prepared by dissolving, or dispersing, a sufficient amount of the dye in water to produce a desired concentration. Water miscible organic solvents can be employed to facilitate dissolution of the dye. In such event, the dye can be dissolved in the solvent then diluted with water. Dispersion of the various ingredients can also be facilitated by heating the composition.

The following examples are offered merely to illustrate the present invention. They are not intended to limit the scope of the invention in any manner.

EXAMPLE 1

2-(4-amino-2-fluoroanilino)ethyltrimethylammonium iodide (II) (35.9 mg) and 5-amino-o-cresol (13.0 mg) were dissolved in 1.0 ml of ethanol and 6.0 ml of water. This solution was mixed with 5.0 ml of H₂O₂ (6%), and pH was adjusted to 9.5 with ammonium hydroxide solution. Blended gray hair was treated with this solution for 30 minutes. A violet color was imparted thereto. Color intensity on hair was weaker when the developer was replaced with 2-(4-amino-2-fluoroanilino)ethyldimethylamine (III) which is the unquaternized dye analog of compound II.

Tristimulus values of the two dyed swatches were determined and are reported hereinbelow:

| Developer used | L | a | b |
|---|---|---|---|
| Compound II (Quaternized) | 15.6 | 4.2 | 1.2 |
| Compound III (Non-quaternized) | 19.6 | 1.8 | 2.7 |

A lower L value is indicative of an increase in intensity. Since such values rae logarithmic in scale, a difference such as obtained herein is visually very evident.

EXAMPLE 2

2-(4-Amino-2-trifluoromethylanilino)ethyltrimethylammonium iodide (IV) (31.4 mg) and 5-amino-o-cresol (13.0 mg.) were dissolved in 1.0 ml of ethanol and 6.0 ml of water. This solution was mixed with 5.0 ml of $H_2O_2$ (6%), and pH was adjusted to 9.5 with ammonium hydroxide solution. Blended gray hair was treated with this solution for 30 minutes. A reddish brown color was imparted thereto. Color intensity on hair was much weaker when the developer was replaced with 2-(4-amino-2-trifluoromethylanilino)ethyldimethylamine (V).

Tristimulus values of two dyed swatches were determined and are reported hereinbelow:

| Developer used | L | a | b |
|---|---|---|---|
| Compound IV (Quaternized) | 22.5 | 9.2 | 5.8 |
| Compound V (Non-quaternized) | 29.1 | 1.3 | 6.6 |

EXAMPLE 3

Example 1 was repeated, except that 2-(4-amino-2-cyano-anilino)ethyltrimethylammonium iodide (VI) (25.7 mg) was used in place of 2-(4-amino-2-fluoroanilino)ethyltrimethylammonium iodide. Blended gray hair was dyed reddish brown. Color intensity on hair was much weaker when the developer was replaced with 2-(4-amino-2-cyanoanilino)ethyldimethylamine (VII).

Tristimulus values of the two dyed swatches were determined and reported hereinbelow:

| Developer used | L | a | b |
|---|---|---|---|
| Compound VI (Quaternized) | 23.2 | 5.7 | 5.4 |
| Compound VII (Non-quaternized) | 26.8 | 3.4 | 5.4 |

EXAMPLE 4

Example 2 was repeated, except that the coupler employed therein was replaced by α-naphthol (18.0 mg). The intermediates were dissolved in 2.0 ml ethyl alcohol and 8.0 ml water. The resultant solution was mixed with 5.0 ml of $H_2O_2$ (6%) and its pH was adjusted to 9.5 with an ammonium hydroxide solution. When the resultant mixture was applied to blended gray hair for 30 minutes, a red-violet color was obtained. The coupler and the non-quaternized developer afforded very little color on hair as indicated by the Tristimulus values which follow:

| Developer used | L | a | b |
|---|---|---|---|
| Compound IV (Quaternized) | 18.9 | 5.4 | 0.3 |
| Compound V (Non-quaternized) | 27.8 | 3.2 | 3.5 |

EXAMPLE 5

2-(4-amino-2-fluoroanilino)ethyltrimethylammonium iodide (II) (49.8 mg) and resorcinol (13.5 mg) were incorporated in 5.0 g of the following formulation:

| | |
|---|---|
| Diethyleneglycol monoethylether | 5 g |
| Oleic acid | 15 g |
| Propylene glycol | 5 g |
| Octoxynol-1 | 7 g |
| Nonoxynol-4 | 3 g |
| Ammonium hydroxide | 9 g |
| EDTA | 0.05 g |
| Water | 13 g |

The mixture was further mixed with 5.0 g of $H_2O_2$ (6%), then used to dye blended gray hair for 30 minutes. A chestnut brown color was imparted to the hair.

Tristimulus values were determined and are reported hereinbelow:

| Developer used | L | a | b |
|---|---|---|---|
| Compound II (Quaternized) | 22.4 | 2.7 | 2.3 |
| Compound III (Non-quaternized) | 22.5 | 3.5 | 2.3 |

Although the L value for the non-quaternized dye was substantially the same as the L value for the quaternized dye, the quaternized dye imparted a desirable chestnut brown color whereas the non-quaternized dye gave a drabber brown.

EXAMPLE 6

The following composition was used to dye blended gray hair for 30 minutes.

2-(4-amino-2-cyanoanilino)ethyltrimethylammonium iodide (VI) 41.8 mg.

| | |
|---|---|
| m-Phenylenediamine | 17.4 mg |
| Nonoxynol-9 | 1.2 mg |
| Nonoxynol-4 | 1.0 g |
| Oleic acid | 0.2 g |
| Propylene glycol | 0.2 g |
| Ethyl alcohol (95%) | 0.5 g |
| EDTA | 0.1 g |
| Sodium bisulfite | 0.02 g |
| Ammonium hydroxide | 0.3 g |
| Water | 1.4 g |

A grayish purple color is obtained on hair. When the non-quaternized developer was used there was no dye uptake. The following table lists the Tristimulus values of the dyeing results.

| Developer used | L | a | b |
|---|---|---|---|
| Compound VI (Quaternized) | 27.6 | 1.2 | 1.5 |
| Compound VII (Non-quaternized) | 30.5 | 0.3 | 3.4 |

What is claimed is:

1. A compound of the formula I:

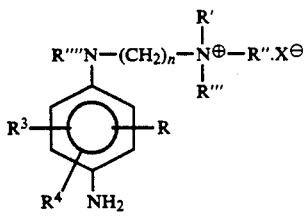

and cosmetically acceptable salts thereof, wherein:

n is an integer from 1 to 6;

$X^-$ is a halide or methylsulfate group;

$R'$, $R''$, $R'''$ are each, independently, $C_{1-6}$ alkyl or $C_{1-6}$ (poly)hydroxyalkyl;

$R''''$ is hydrogen, $C_{1-6}$ alkyl or $C_{1-6}$ (poly)hydroxyalkyl;

R is F, $CF_3$ or CN; and $R^3$ and $R^4$ are each, independently, hydrogen, $C_{1-6}$ alkyl, halogen or $C_{1-6}$ alkoxy.

2. The compound of claim 1, wherein n is 2.

3. The compound of claim 2, wherein X is iodide.

4. The compound of claim 3, wherein $R^3$ and $R^4$ are hydrogen.

5. The compound of claim 4, wherein $R'$, $R''$, and $R'''$ are methyl.

6. The compound of claim 5, wherein $R''''$ is hydrogen.

7. The compound of claim 1, selected from the group consisting of:
2-(4-amino-2-fluoroanilino)ethyltrimethylammonium iodide,
2-(4-amino-2-trifluoromethylanilino)ethyltrimethylammonium iodide, and
2-(4-amino-2-cyano-anilino)ethyltrimethylammonium iodide.

* * * * *